United States Patent
Kang et al.

(10) Patent No.: US 7,910,780 B2
(45) Date of Patent: Mar. 22, 2011

(54) METHOD FOR PURIFYING TEREPHTHALALDEHYDE

(75) Inventors: Seong Hoon Kang, Daejeon (KR); In Kyu Park, Daejeon (KR); Yeong Dae Kim, Daejeon (KR); Jong Suh Park, Chungcheongnamdo (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 12/312,374

(22) PCT Filed: Nov. 15, 2007

(86) PCT No.: PCT/KR2007/005728
§ 371 (c)(1),
(2), (4) Date: Jan. 20, 2010

(87) PCT Pub. No.: WO2008/060107
PCT Pub. Date: May 22, 2008

(65) Prior Publication Data
US 2010/0130791 A1   May 27, 2010

(30) Foreign Application Priority Data

Nov. 16, 2006   (KR) .................. 10-2006-0113505

(51) Int. Cl.
*C07C 45/90* (2006.01)
(52) U.S. Cl. ........................................ 568/438
(58) Field of Classification Search .................. 568/438
See application file for complete search history.

(56) References Cited

U.S. PATENT DOCUMENTS

| 4,017,547 | A | 4/1977 | Simmons et al. |
| 6,891,069 | B1 | 5/2005 | Zhu et al. |
| 7,183,442 | B2 * | 2/2007 | Yoon et al. .................... 568/438 |
| 7,714,173 | B2 * | 5/2010 | Kang et al. .................... 568/437 |

FOREIGN PATENT DOCUMENTS

JP          60039183 A     2/1985

* cited by examiner

*Primary Examiner* — Sikarl A Witherspoon
(74) *Attorney, Agent, or Firm* — McKenna Long & Aldridge LLP

(57) ABSTRACT

The present invention relates to a method for purifying terephthalaldehyde which comprises a first step of dissolving terephthalaldehyde containing impurities in an aromatic solvent at high temperature to prepare a solution; and a second step of quenching the solution to re-crystallize it into terephthalaldehyde. In accordance with the present invention, high pure terephthalaldehyde may be economically prepared.

11 Claims, No Drawings

METHOD FOR PURIFYING TEREPHTHALALDEHYDE

This application is a 35 U.S.C. §371 National Stage entry of International Application No. PCT/KR2007/005728, filed on Nov. 15, 2007, and claims the benefit of Korean Application No. 10-2006-0113505, filed on Nov. 16, 2006 which is hereby incorporated by reference in its entirety.

TECHNICAL FIELD

The present invention relates to a method for purifying terephthalaldehyde. Particularly, the present invention relates to a method for purifying terephthalaldehyde which comprises a first step of dissolving terephthalaldehyde containing impurities in an aromatic solvent at high temperature to prepare a solution; and a second step of quenching the solution to re-crystallize it into terephthalaldehyde.

BACKGROUND ART

Aromatic aldehydes have aldehyde groups with a high reactivity, so that they may be employed in a wide variety of uses. Especially, terephthalaldehydes having two aldehyde groups at para-positions as Formula 1 below are noted for basic raw materials such as medicinal products, agrichemicals, pigments, liquid crystal polymers, electro-conductive polymers, and heat-resistant plastics.

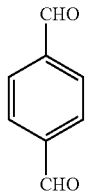

1

Said terephthalaldehyde of Formula 1 is a sublimable white solid having a molecular weight of 134.13 and a melting point of 114-116° C. It is known that it is well dissolved in alcohols, and is also dissolved in ethers, alkali solutions and hot water.

Terephthalaldehyde as a raw material of the present invention is prepared by the known methods, which are briefly described below.

In the methods for preparing terephthalaldehyde, there is a method for dehydrating intermediates obtained via chlorination, a method for hydrogenating methylterephthalate, or a method for preparing terephthalate by oxidating p-xylene in vapor phase, etc.

In order to use terephthalaldehyde as a raw material in a polymer synthesis or a fine chemical process, it should be purified to a high purity, for which impurities contained in terephthalaldehyde, such as benzaldehyde, p-tolualdehyde, 4-hydroxybenzaldehyde and the like, have to be removed.

Until now, there is almost no example reported for the method for preparing a high purity terephthalaldehyde which may be used in the polymer synthesis or the fine chemical process by efficiently removing impurities produced in the synthesis of terephthalaldehyde.

U.S. Pat. No. 2,888,488 discloses a method for preparing terephthalaldehyde which includes solvent extracting-drying-subliming as a purification process. This method has, however, problems that its procedures are complicated and a non-environment friendly compound, chloroform, is used as a solvent.

JP Unexamined Patent Publication No. 2001-199910 discloses a method for re-crystallizing aromatic aldehydes by a cooling process. This method is also limited to obtaining a high purity terephthalaldehyde.

DISCLOSURE OF THE INVENTION

The object of the present invention is intended to solve the problems above, and is to provide a method for purifying a low pure terephthalaldehyde, including terephthalaldehyde and a small quantity of impurities obtained through a conventional method, into a high pure terephthalaldehyde.

The present invention relates to a method for purifying terephthalaldehyde which comprises a first step of dissolving terephthalaldehyde containing impurities in an aromatic solvent at high temperature to prepare a solution; and a second step of quenching the solution to re-crystallize it into terephthalaldehyde.

BEST MODE FOR CARRYING OUT THE INVENTION

The present invention is explained in detail below.

The impurity-containing crude terephthalaldehydes used herein are not specifically limited, and include terephthalaldehydes which are prepared by the known methods or commercially available terephthalaldehydes.

The present invention is characterized by dissolving crude terephthalaldehyde in an aromatic solvent and quenching the solution to re-crystallize it into terephthalaldehyde. Said aromatic solvent is preferably benzene, toluene, xylene or a mixture thereof, and more preferably xylene. Since xylene, especially p-xylene, is a raw material in a method for preparing terephthalaldehyde in a gas phase oxidation, it is desired in aspects of economic efficiency and processability.

In addition, the first step of dissolving terephthalaldehyde containing impurities in an aromatic solvent at high temperature to prepare a solution is allowed to subject to a method of directly dissolving terephthalaldehyde in an aromatic solvent at high temperature, but it preferably includes, in an aspect of easiness of process, a step of mixing terephthalaldehyde with an aromatic solvent at room temperature and a step of increasing the mixture to a temperature of 70 to 120° C. If said temperature is less than 70° C., it is apprehended that terephthalaldehyde is not sufficiently dissolved. If said temperature is in excess of 120° C., the process is disadvantageous due to overheating.

The amount of said aromatic solvent is not limited, but it is especially preferred that the amount is dissolved in a range near a solubility for terephthalaldehyde crystals to melt at the specific high temperature. More preferably, the amount is such that a weight ratio of terephthalaldehyde containing impurities to an aromatic solvent is 1:2 to 10. If the weight ratio is less than 2, the purity may be lowered. If the weight ratio is in excess of 10, waste water may be increased.

In addition, to prevent impurities from being precipitated during the quenching procedure in the second step, a solvent for impurities of terephthalaldehyde is preferably added to the aromatic solvent. The solvent for impurities may be used without any limitation, as long as it has not so different solubility depending on temperature, but has a large solubility for impurities. Usable solvents are preferably dimethylsulfoxide (DMSO), N,N-dimethylformamide (DMF), N,N-dimethylacetamide (DMAc), N-methyl-2-pyrrolidone (NMP), tetrahydrofuran (THF), acetone, acetonitrile or a mixture thereof, and more preferably dimethylsulfoxide (DMSO).

The amounts of the aromatic solvent and the solvent for impurities to be used may be appropriately regulated depending on target recovery rate and purity of terephthalaldehyde. Especially, the weight ratio of the aromatic solvent to the solvent for impurities is preferably 1:0.02 to 0.2, and more preferably 1:0.05 to 0.1. If said weight ratio is less than 0.02, the purity may be lowered. If the ratio is more than 0.2, the recovery rate may be lowered and waste water may be increased.

On the one hand, the temperature of adding the solvent for impurities is not specifically limited. That is, it may be added to p-xylene at room temperature, and then the mixture be raised to high temperature to dissolve terephthalaldehyde, or it may be added to p-xylene at high temperature, in which terephthalaldehyde is dissolved. To prevent the solvent for impurities from being volatilized and lost, it is preferred to add or add it dropwise to an aromatic solvent at high temperature.

The second step of quenching a solution comprising terephthalaldehyde and an aromatic solvent to re-crystallize it into terephthalaldehyde is not specifically limited, but it is to quench the solution to 40° C. or less, more preferably, room temperature, under stirring. The quenching may be utilized by usual cooling means or standing to cool.

In addition, the re-crystallized terephthalaldehyde above may be subsequently filtered, and dried to afford the finally re-crystallized terephthalaldehyde. At this time, drying may be practiced using a usual drying method such as an oven drying or a vacuum drying, with appropriately regulating temperature and time of drying. Especially, it is preferred to dry at 40 to 60° C. for 20 to 28 hours.

The physical properties of p-xylene, a usable aromatic solvent herein, and dimethylsulfoxide (DMSO), a solvent for impurities, and their solubility of terephthalaldehyde and major impurities are represented in Table 1 below.

TABLE 1

| | | p-xylene (25° C.) | p-xylene (100° C.) | DMSO (25° C.) |
|---|---|---|---|---|
| Property | Specific Gravity | 0.86 | | 1.1 |
| | Boiling Point (° C.) | 138 | | 189 |
| | Melting Point ((° C.) | 13 | | 18.4 |
| Solubility | 4-CBA | <2 | <20 | 1000 |
| | 4-HBA | <2 | <20 | 1000 |
| | TPA | <5 | <20 | 50 |
| | BA | <5 | 500 | 500 |
| | HQ | <5 | <5 | 1000 |
| | Crude TPAL | 25 | 200 | 200 |
| | Ald. TPAL | 25 | 200 | 200 |

Unit of solubility: g/L
[p-tolualdehyde (PTAL) and benzaldehyde (BAL) are in liquid at room temperature]
4-CBA: 4-carboxybenzaldehyde
4-HBA: 4-hydroxybenzaldehyde
TPA: terephthalic acid
BA: benzoic acid
HQ: hydroquinone
Crude TPAL: pre-purified terephthalaldehyde
Ald. TPAL: Aldrich agent terephthalaldehyde In addition, when the desired terephthalaldehyde is in high purity, the step of purifying terephthalaldehyde as above may be, of course, repeated two or more times.

To assist understanding of the present invention, the preferred examples are shown below. However, these examples are intended to illustrate the present invention, whose scope is not limited to these examples.

EXAMPLES

Example 1

10 g of pre-purified terephthalaldehyde was added to 50 g of p-xylene at room temperature and completely dissolved, with well stirring and slowly heating to 100° C. This solution was cold to room temperature, with again well stirring. After left for 1 hour, the resulting product was filtered and dried at 40° C. for 24 hours to obtain the re-crystallized terephthalaldehyde.

Purities of terephthalaldehyde before and after purification were measured by a gas chromatography with mass selective detector (GC-MSD). Terephthalaldehyde used in purification was identified to be a purity of 97.9 wt % by GC-MSD. In the following examples, terephthalaldehyde with the same purity was used and purified.

Purity and yield of terephthalaldehyde after purification were represented in Table 2 below.

Example 2

10 g of pre-purified terephthalaldehyde was added to 50 g of p-xylene at room temperature and completely dissolved, with well stirring and slowly heating to 100° C. To this solution was added 1 g of dimethylsulfoxide (weight ratio of p-xylene to dimethylsulfoxide=1:0.02). This solution was cold to room temperature, with again well stirring. After left for 1 hour, the resulting product was filtered and dried at 40° C. for 24 hours to obtain the re-crystallized terephthalaldehyde.

Purity and yield of terephthalaldehyde after purification were represented in Table 2 below.

Example 3

Terephthalaldehyde was purified by the same method as Example 2 except that 2.5 g of dimethylsulfoxide was added (weight ratio of p-xylene to dimethylsulfoxide=1:0.05). Purity of the obtained terephthalaldehyde was determined by GC-MSD.

Purity and yield of terephthalaldehyde were represented in Table 2 below.

Example 4

Terephthalaldehyde was purified by the same method as Example 2 except that 5 g of dimethylsulfoxide was added (weight ratio of p-xylene to dimethylsulfoxide=1:0.1). Purity of the obtained terephthalaldehyde was determined by GC-MSD.

Purity and yield of terephthalaldehyde were represented in Table 2 below.

Example 5

Terephthalaldehyde was purified by the same method as Example 2 except that 10 g of dimethylsulfoxide was added (weight ratio of p-xylene to dimethylsulfoxide=1:0.2). Purity of the obtained terephthalaldehyde was determined by GC-MSD.

Purity and yield of terephthalaldehyde were represented in Table 2 below.

Example 6

5 g of pre-purified terephthalaldehyde was added to 25 g of p-xylene at room temperature and completely dissolved, with well stirring and slowly heating to 90° C. To this solution was added 0.5 g of dimethylsulfoxide (weight ratio of p-xylene to dimethylsulfoxide=1:0.02). This solution was cold to room temperature, with again well stirring. After left for 1 hour, the resulting product was filtered and dried at 40° C. for 24 hours to obtain the re-crystallized terephthalaldehyde.

Purity and yield of terephthalaldehyde after purification were represented in Table 2 below.

Example 7

Terephthalaldehyde was purified by the same method as Example 6 except that 1 g of dimethylsulfoxide was added (weight ratio of p-xylene to dimethylsulfoxide=1:0.04). Purity of the obtained terephthalaldehyde was determined by GC-MSD.

Purity and yield of terephthalaldehyde were represented in Table 2 below.

Example 8

Terephthalaldehyde was purified by the same method as Example 6 except that 1.25 g of dimethylsulfoxide was added (weight ratio of p-xylene to dimethylsulfoxide=1:0.05). Purity of the obtained terephthalaldehyde was determined by GC-MSD.

Purity and yield of terephthalaldehyde were represented in Table 2 below.

Example 9

Terephthalaldehyde was purified by the same method as Example 6 except that 1.5 g of dimethylsulfoxide was added (weight ratio of p-xylene to dimethylsulfoxide=1:0.06). Purity of the obtained terephthalaldehyde was determined by GC-MSD. Purity and yield of terephthalaldehyde were represented in Table 2 below.

Example 10

Terephthalaldehyde was purified by the same method as Example 6 except that 2 g of dimethylsulfoxide was added (weight ratio of p-xylene to dimethylsulfoxide=1:0.08). Purity of the obtained terephthalaldehyde was determined by GC-MSD. Purity and yield of terephthalaldehyde were represented in Table 2 below.

Example 11

10 g of pre-purified terephthalaldehyde was added to 50 g of toluene at room temperature and completely dissolved, with well stirring and slowly heating to 100° C. To this solution was added 10 g of dimethylsulfoxide (weight ratio of toluene to dimethylsulfoxide=1:0.2). This solution was cold to room temperature, with again well stirring. After left for 1 hour, the resulting product was filtered and dried at 40° C. for 24 hours to obtain the re-crystallized terephthalaldehyde.

Purity and yield of terephthalaldehyde after purification were represented in Table 2 below.

Comparative Example 1

5 g of pre-purified terephthalaldehyde was added to 25 g of methanol at room temperature and completely dissolved, with well stirring and slowly heating to 60° C. This solution was cold to 0° C., with again well stirring. After left for 1 hour, the resulting product was filtered and dried at 40° C. for 24 hours to obtain the re-crystallized terephthalaldehyde.

Purity and yield of terephthalaldehyde after purification were represented in Table 2 below.

Comparative Example 2

2 g of pre-purified terephthalaldehyde was added to 100 g of ethyl acetate at room temperature and completely dissolved, with well stirring and slowly heating to 70° C. This solution was cold to room temperature, with again well stirring. After left for 1 hour, the resulting product was filtered and dried at 40° C. for 24 hours to obtain the re-crystallized terephthalaldehyde.

Purity and yield of terephthalaldehyde after purification were represented in Table 2 below.

TABLE 2

| Class | Solvent | Solvent:DMSO | Solution Temperature (° C.) | Yield of TPAL (%) | Purity after Purification (%) |
| --- | --- | --- | --- | --- | --- |
| Example 1 | p-xylene | — | 100 | 95.4 | 98.3 |
| Example 2 | p-xylene | 1:0.02 | 100 | 95.1 | 98.4 |
| Example 3 | p-xylene | 1:0.05 | 100 | 88.7 | 98.7 |
| Example 4 | p-xylene | 1:0.1 | 100 | 78.7 | 99.5 |
| Example 5 | p-xylene | 1:0.2 | 100 | 70.2 | 99.4 |
| Example 6 | p-xylene | 1:0.02 | 90 | 94.8 | 98.5 |
| Example 7 | p-xylene | 1:0.04 | 90 | 89.8 | 98.3 |
| Example 8 | p-xylene | 1:0.05 | 90 | 87.3 | 98.4 |
| Example 9 | p-xylene | 1:0.06 | 90 | 83.4 | 98.3 |
| Example 10 | p-xylene | 1:0.08 | 90 | 81.6 | 98.9 |
| Example 11 | Toluene | 1:0.2 | 100 | 75.8 | 98.7 |
| Com. Exam. 1 | Methanol | — | 60 | 41 | 98.2 |
| Com. Exam. 2 | Ethyl acetate | — | 70 | 68 | 98.0 |

As shown in Table 2 above, the aromatic solvent according to the present invention may afford terephthalaldehyde with higher purity over aliphatic alcohol-based solvents or ester-based solvents. Especially, in case of increasing the added amount of dimethylsulfoxide, terephthalaldehyde with higher purity may be obtained over the quenching purification using p-xylene only as a solvent.

INDUSTRIAL APPLICABILITY

The method for purifying terephthalaldehyde of the present invention may use an aromatic solvent to obtain terephthalaldehyde with high purity in a high yield, with an economical and simple method, and use dimethylsulfoxide, a solvent for impurities, to economically purify high pure terephthalaldehyde, which cannot obtain by simple quenching re-crystallization.

The above description is explained in detail only about embodiments of the present invention. However, it is apparent to one skilled in this field that various modifications and changes are available within the technical concepts of the present invention. Such modifications and changes should be fallen within the appended claims.

The invention claimed is:

1. A method for purifying terephthalaldehyde which comprises
    a first step of dissolving terephthalaldehyde containing impurities in an aromatic solvent at high temperature to prepare a solution; and
    a second step of quenching the solution to re-crystallize it into terephthalaldehyde.

2. The method for purifying terephthalaldehyde of claim 1, wherein the aromatic solvent is benzene, toluene, xylene or a mixture thereof.

3. The method for purifying terephthalaldehyde of claim 2, wherein the aromatic solvent is p-xylene.

4. The method for purifying terephthalaldehyde of claim 1, wherein the weight ratio of terephthalaldehyde containing impurities to the aromatic solvent is 1:2 to 10.

5. The method for purifying terephthalaldehyde of claim 1, wherein a solvent for impurities selected from dimethylsulfoxide (DMSO), N,N-dimethylformamide (DMF), N,N-dimethylacetamide (DMAc), N-methyl-2-pyrrolidone (NMP), tetrahydrofuran (THF), acetone, acetonitrile or a mixture thereof is added to the aromatic solvent.

6. The method for purifying terephthalaldehyde of claim 5, wherein the solvent for impurities is dimethylsulfoxide (DMSO).

7. The method for purifying terephthalaldehyde of claim 5, wherein the weight ratio of the aromatic solvent to the solvent for impurities is 1:0.02 to 0.2.

8. The method for purifying terephthalaldehyde of claim 7, wherein the weight ratio of the aromatic solvent to the solvent for impurities is 1:0.05 to 0.1.

9. The method for purifying terephthalaldehyde of claim 5, wherein the solvent for impurities is added to the aromatic solvent at high temperature.

10. The method for purifying terephthalaldehyde of claim 1, wherein it further comprises a step of drying the re-crystallized terephthalaldehyde.

11. The method for purifying terephthalaldehyde of claim 10, wherein the re-crystallized terephthalaldehyde is filtered and dried at 40 to 60° C. for 20 to 28 hours.

* * * * *